(12) United States Patent
Zilbershlag

(10) Patent No.: US 8,579,789 B1
(45) Date of Patent: Nov. 12, 2013

(54) ENDOVASCULAR VENTRICULAR ASSIST DEVICE, USING THE MATHEMATICAL OBJECTIVE AND PRINCIPLE OF SUPERPOSITION

(75) Inventor: Michael Zilbershlag, Givat Shmuel (IL)

(73) Assignee: Leviticus Cardio Ltd., Givat Shmuel (IL)

( * ) Notice: Subject to any disclaimer, the term of this patent is extended or adjusted under 35 U.S.C. 154(b) by 417 days.

(21) Appl. No.: 12/887,536

(22) Filed: Sep. 22, 2010

Related U.S. Application Data

(60) Provisional application No. 61/245,048, filed on Sep. 23, 2009.

(51) Int. Cl.
- A61N 1/00 (2006.01)
- A61N 1/362 (2006.01)
- A61B 5/02 (2006.01)

(52) U.S. Cl.
USPC ............ 600/16; 600/15; 600/17; 607/34

(58) Field of Classification Search
USPC .................. 600/15–17, 504; 607/34
See application file for complete search history.

(56) References Cited

U.S. PATENT DOCUMENTS

| | | | |
|---|---|---|---|
| 4,906,229 A | 3/1990 | Wampler | |
| 4,957,504 A | 9/1990 | Chardack | |
| 5,749,855 A | 5/1998 | Reitan | |
| 6,421,889 B1 | 7/2002 | Chien | |
| 6,527,699 B1 | 3/2003 | Goldowsky | |
| 6,772,011 B2 | 8/2004 | Dolgin | |
| 7,613,497 B2 | 11/2009 | Govari et al. | |
| 7,650,192 B2 | 1/2010 | Wahlstrand | |
| 7,741,734 B2 | 6/2010 | Joannopoulos et al. | |
| 7,825,543 B2 | 11/2010 | Karalis et al. | |
| 7,825,776 B2 | 11/2010 | Smith et al. | |
| 7,956,725 B2 | 6/2011 | Smith | |
| 8,075,472 B2 | 12/2011 | Zilbershlag et al. | |
| 8,244,367 B2 | 8/2012 | Wahlstrand et al. | |
| 8,285,388 B2 | 10/2012 | Wahlstrand | |
| 2004/0014315 A1 | 1/2004 | Lai et al. | |
| 2004/0054251 A1* | 3/2004 | Liotta | 600/17 |
| 2004/0115038 A1 | 6/2004 | Nuesser et al. | |
| 2005/0220636 A1 | 10/2005 | Henein et al. | |
| 2007/0132587 A1 | 6/2007 | Smith et al. | |
| 2007/0182578 A1 | 8/2007 | Smith | |
| 2008/0041930 A1 | 2/2008 | Smith et al. | |
| 2008/0238680 A1 | 10/2008 | Posamentier et al. | |
| 2009/0243813 A1 | 10/2009 | Smith et al. | |
| 2010/0045114 A1 | 2/2010 | Sample et al. | |
| 2010/0052811 A1 | 3/2010 | Smith et al. | |
| 2010/0076247 A1 | 3/2010 | Zilbershlag et al. | |
| 2010/0081379 A1 | 4/2010 | Cooper et al. | |
| 2010/0187913 A1 | 7/2010 | Smith et al. | |

* cited by examiner

Primary Examiner — Nicole F Lavert
(74) Attorney, Agent, or Firm — Brown Rudnick LLP

(57) ABSTRACT

This embodiment suggests new approach for Endovascular Ventricular Assist Device, using the mathematical objective & principle of superposition allow design and calculation of the body response to VAD pump located in the Aorta. This new approach allows minimal invasive Endovascular VAD that result in similar relief to the heart as partial VAD. Using special power transfer technique will allow wireless power transformation into the aorta. This methods and technique should dramatic reduce VAD barrier.

4 Claims, 16 Drawing Sheets human vascular hemodinamic system with pump

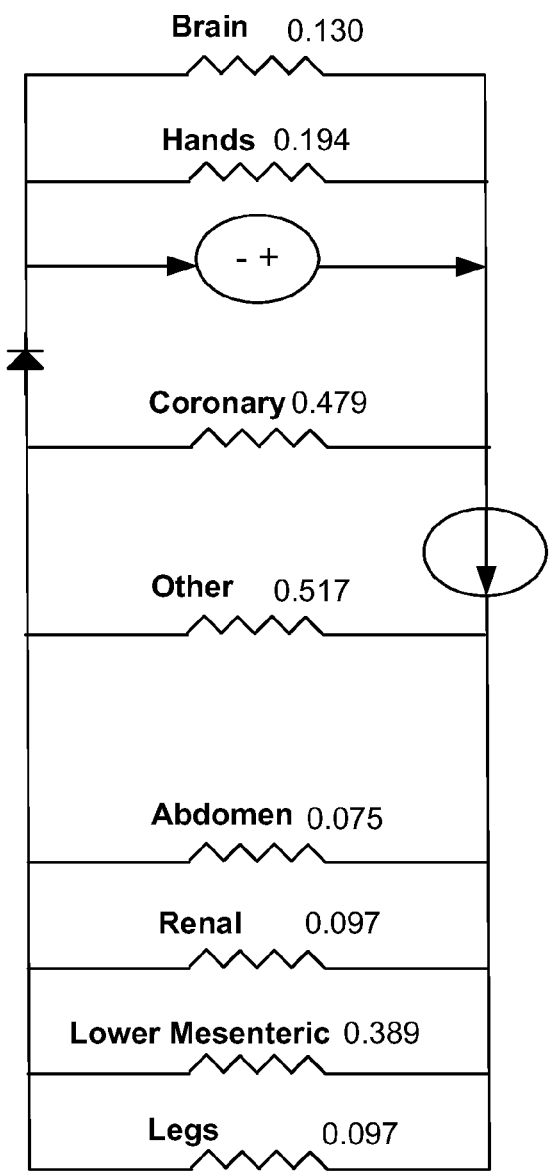
Figure 1 - electrical circuits that resemble the human vascular system

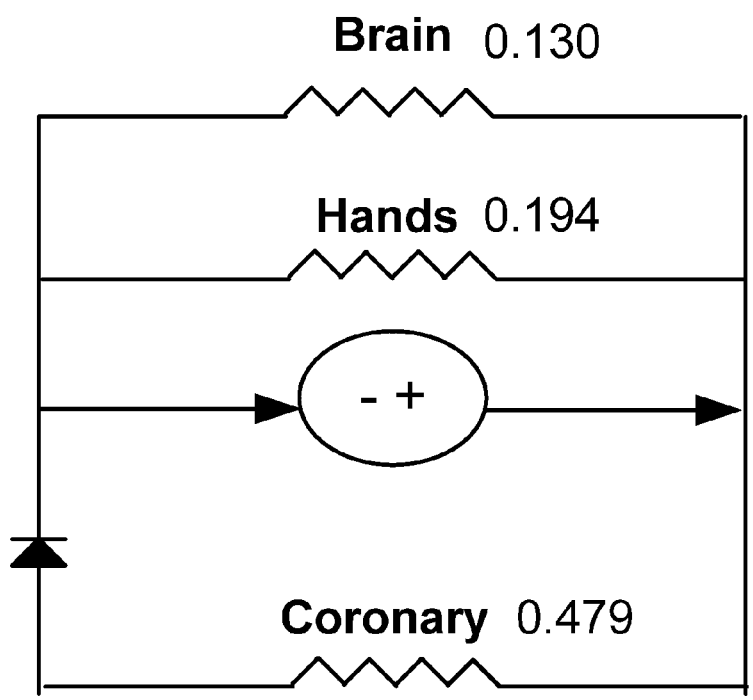
Figure 2 – The heart supply only to the upper body - the main organ

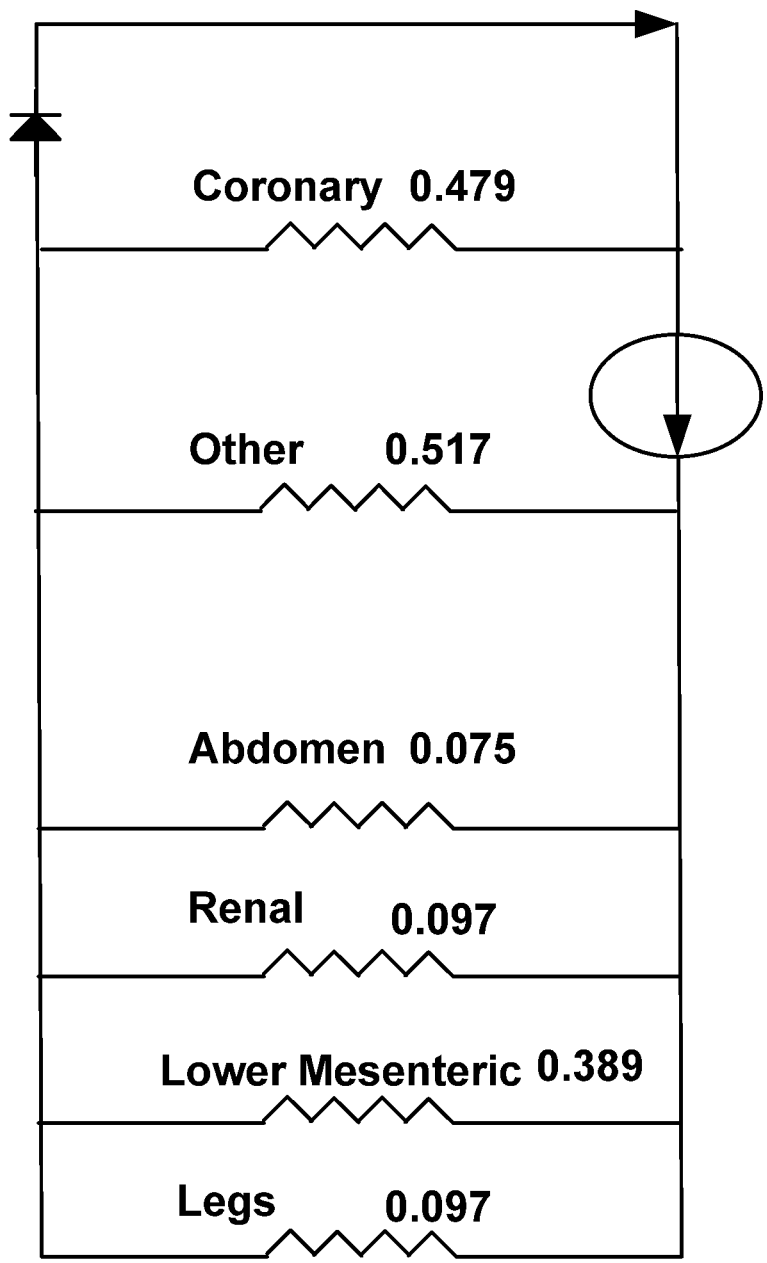
Figure 3 - the lower body organs

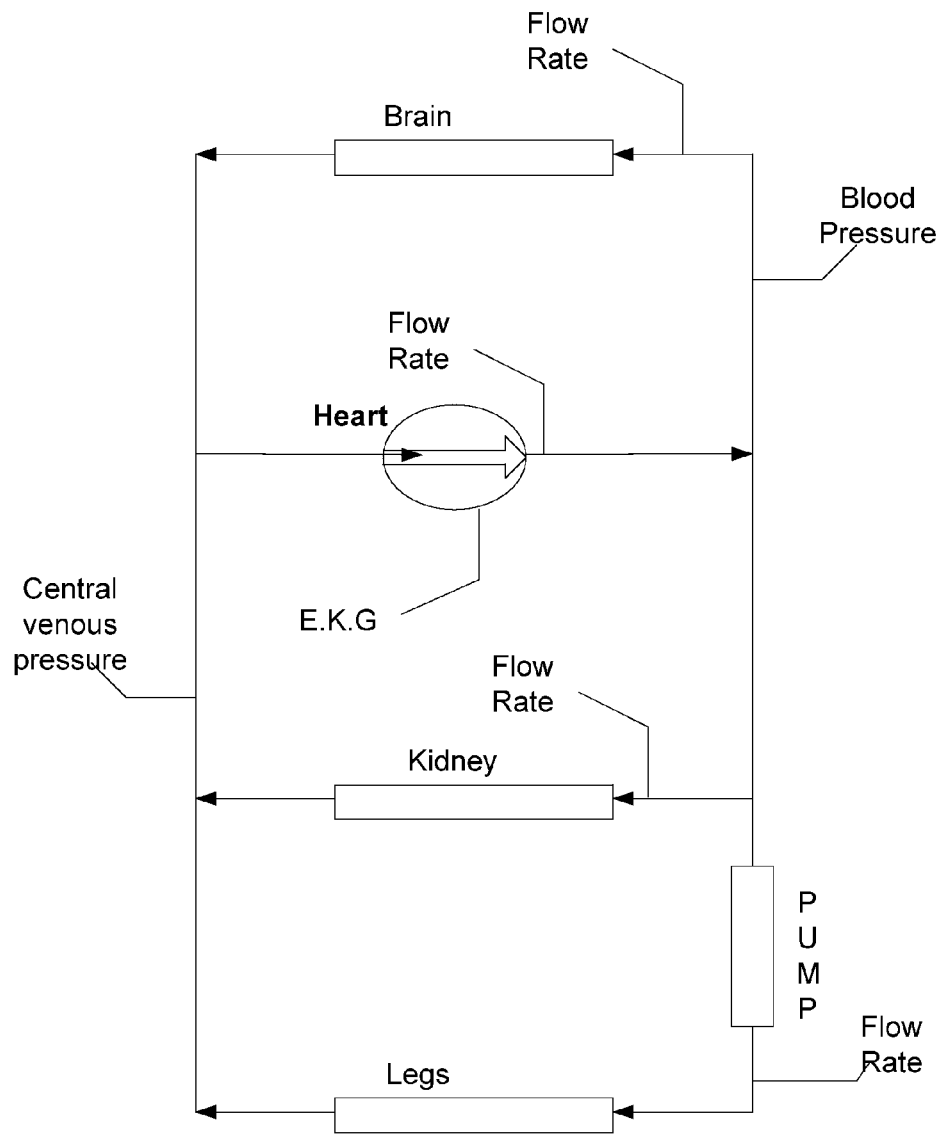
Figure 4 - human vascular hemodinamic system with pump

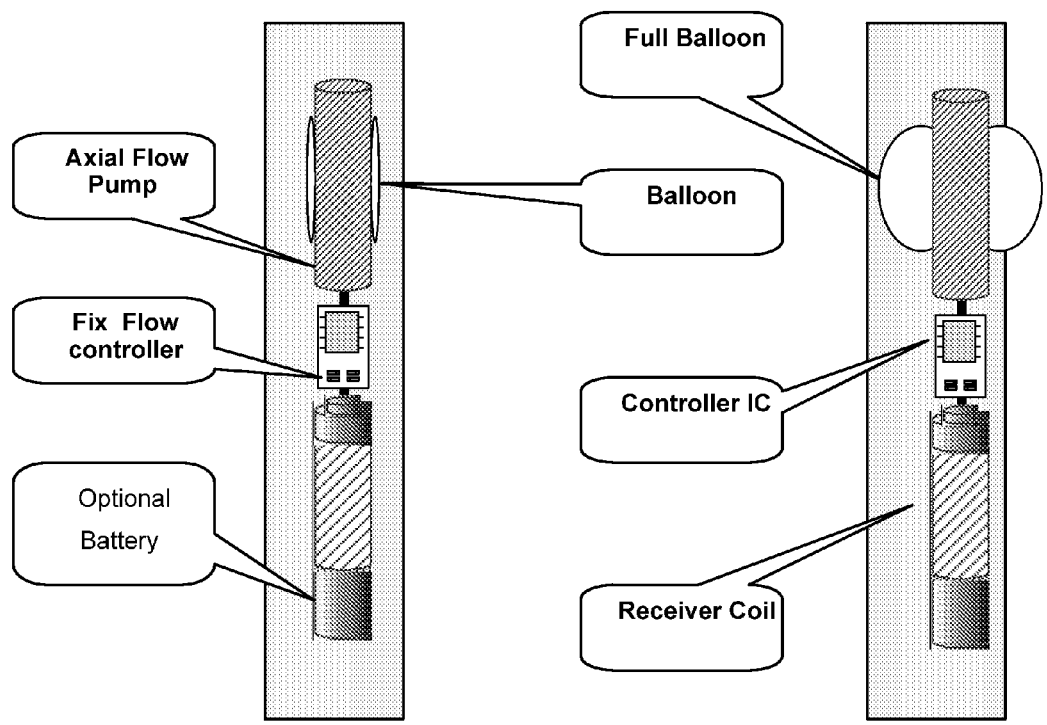
Figure 5 - powered from out side the body using coil as power receiver

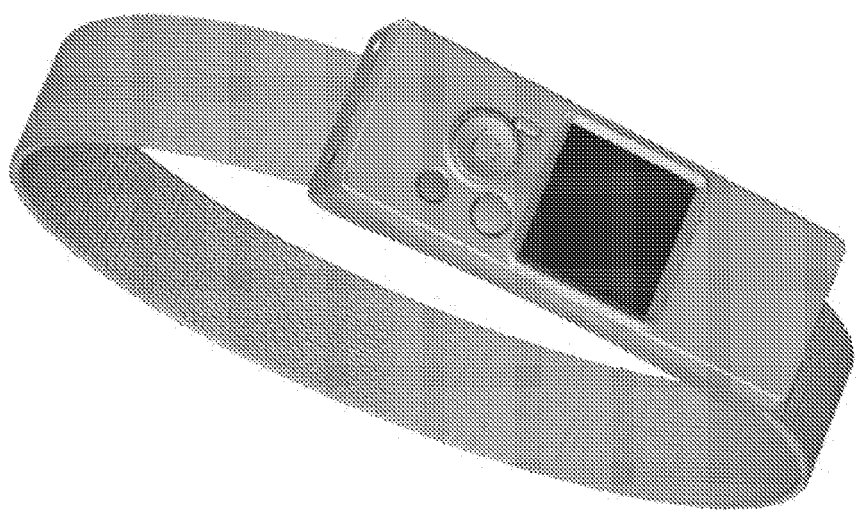
Figure 6 - powered from out side the body using power belt

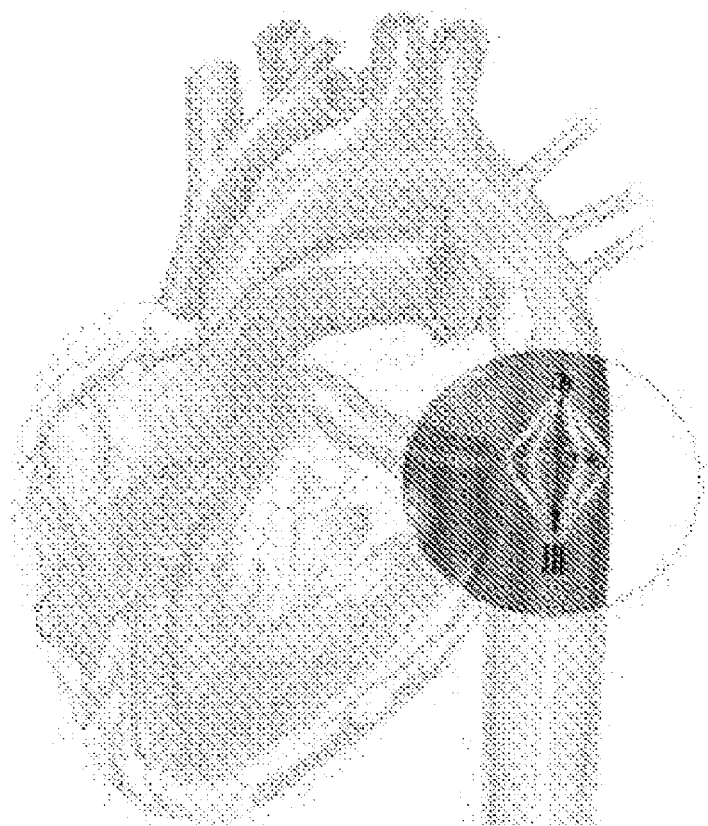
Figure7 – Cardio Bridge location

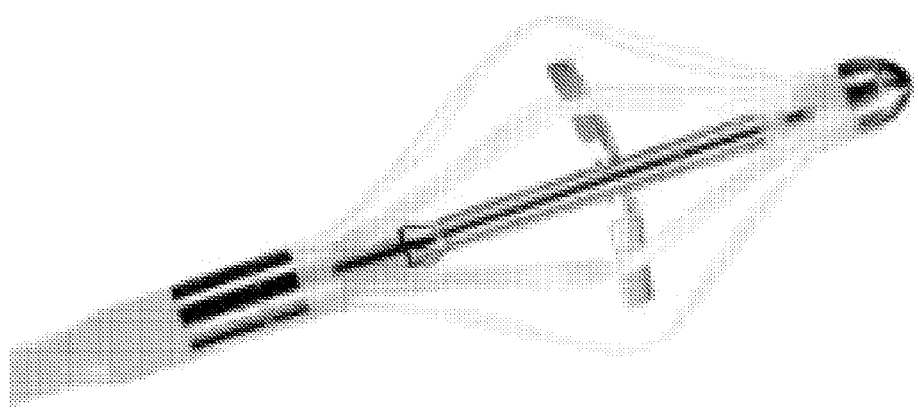
Figure 8 – Cardio Bridge Pump

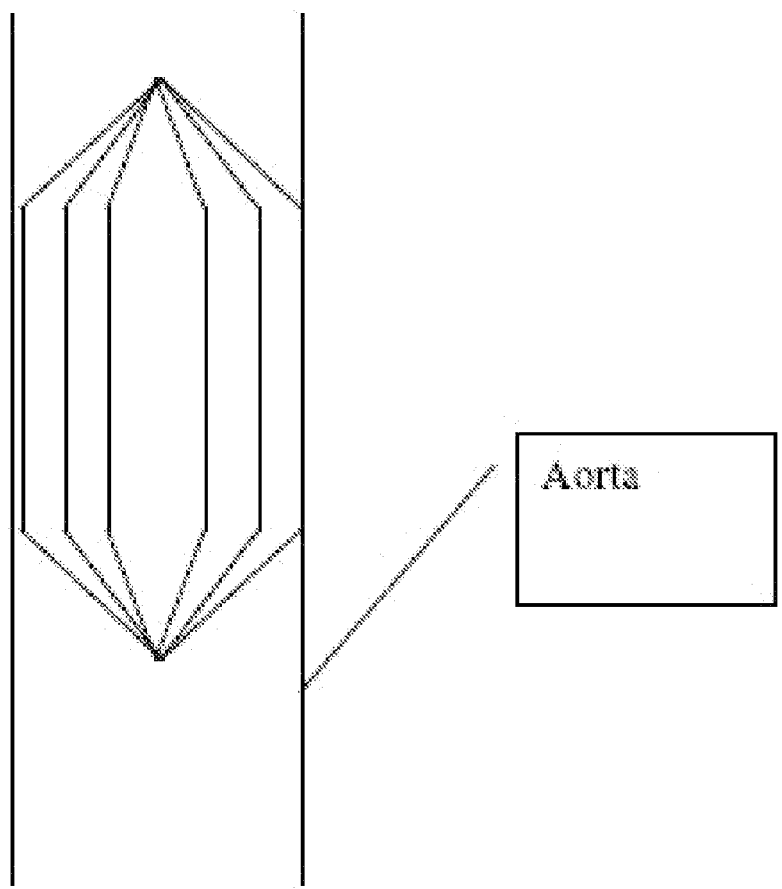
Figure 9 - longer fixation

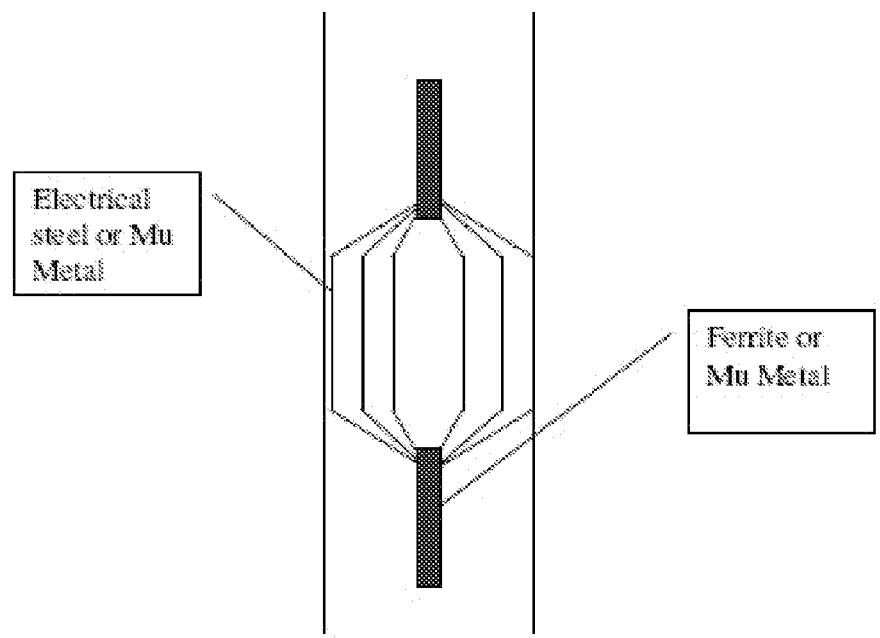
Figure 10 – Magnetic capability & fixation

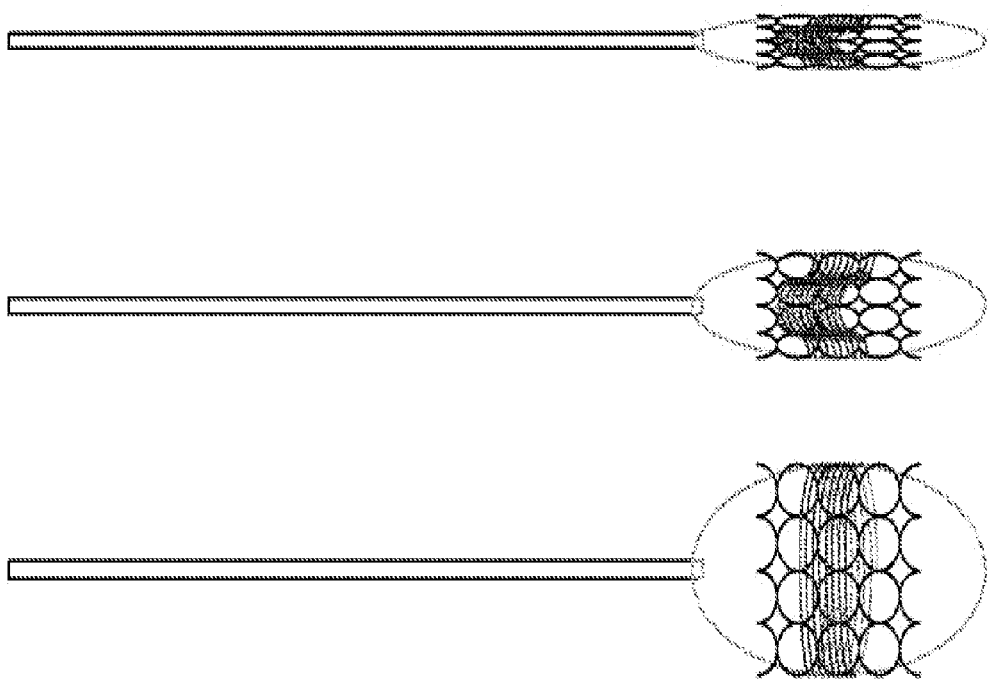
Figure 11 – fixation and power receiver option

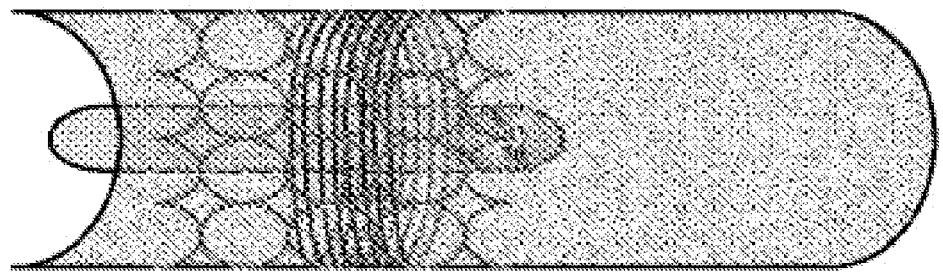
Figure 12 – extract the coil to aorta dimension

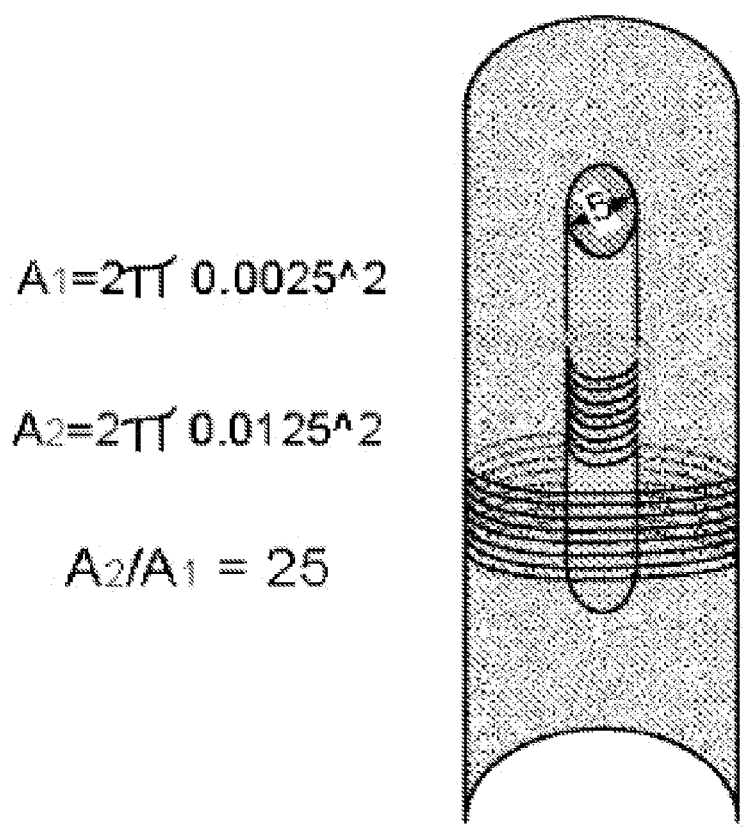
Figure 13 – The relation between the coils diameter to the receiver capability

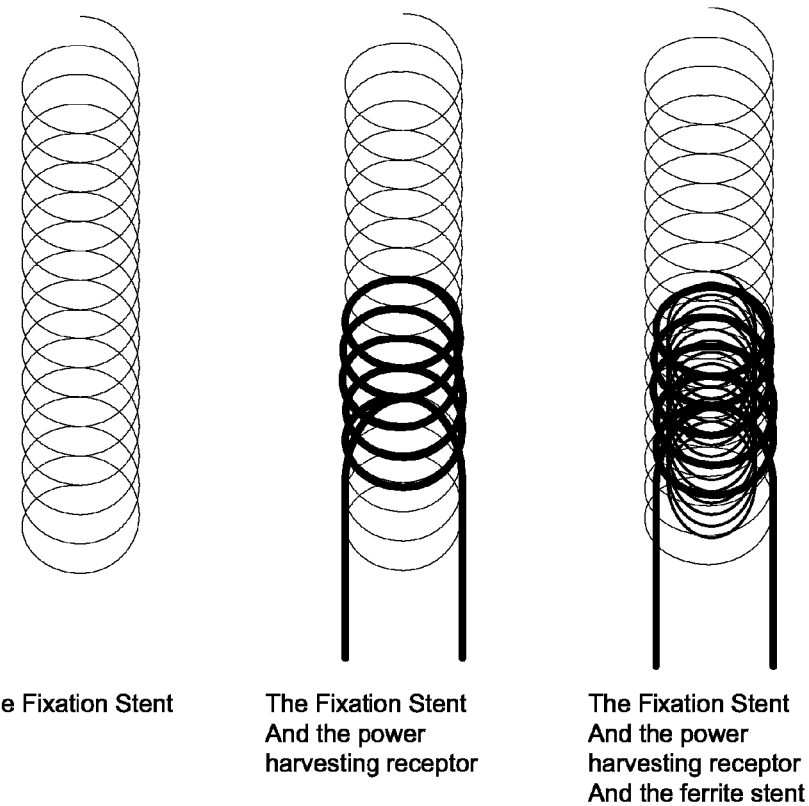
Figure 14 – The three stages of stent installation

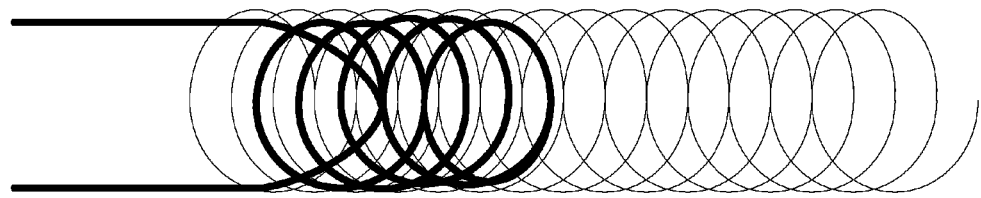
One mesh-weave stent fixation and power harvesting receptor weaved together
Figure -15 – One Weave stent that use some of its wire as power receiver

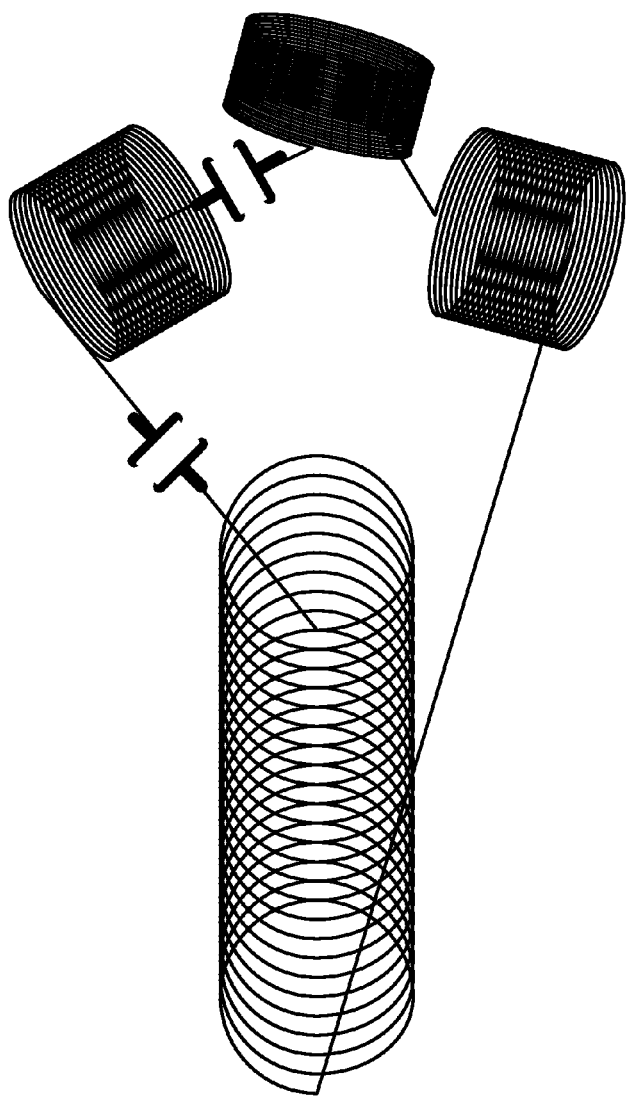
Figure 16 - migration from Vertical magnetic power to tri Horizontal AC motor coils

ENDOVASCULAR VENTRICULAR ASSIST DEVICE, USING THE MATHEMATICAL OBJECTIVE AND PRINCIPLE OF SUPERPOSITION

CROSS-REFERENCE TO RELATED APPLICATIONS

This application draws priority from U.S. Patent Application Ser. No. 61/245,048 filed Sep. 23, 2009, which is hereby incorporated by reference for all purposes as if fully set forth herein.

BACKGROUND

The following published patent documents provide potentially relevant background art, and are each incorporated herein by reference in their entirety: U.S. Pat. No. 6,421,889; PCT/IL2008/000604 which is now WO 2008/135988A2; U.S. Pat. No. 4,906,229; US 2004/0143151 which is now U.S. Pat. No. 7,470,246; U.S. Pat. No. 4,957,504; U.S. Pat. No. 6,527,699; US 2004/0115038 which is now U.S. Pat. No. 7,467,929; U.S. Pat. No. 5,749,855; U.S. application Ser. No. 12/527,595 which is now U.S. Pat. No. 8,075,472.

DISCUSSION OF EMBODIMENTS

The following abbreviations are used in the present document: CHF Congestive heart failure, VAD—ventricular assist device and EVAD—Endovascular VAD.

Congestive heart failure (CHF), or just heart failure, is the pathophysiologic state in which the heart, via an abnormality of cardiac function, fails to pump blood at a rate commensurate with the requirements of the metabolizing tissues. Heart failure may be caused by cardiomyopathy, heart valves damage, coronary heart disease, hypertension or in some cases diabetes. The heart compensates for the pumping insufficiency by dilating the ventricular chambers, thickening the walls (hypertrophy), and accelerating the pulsation rates.

More than 11 million patients currently suffer from CHF worldwide with a annual increase of about 10% of cases. Approximately 1 million patients present severe CHF conditions, and 1% are admitted in terminal condition. Nowadays, CHF is considered as the fastest-growing clinical cardiac disease entity in the United States, affecting 2% of the population. Nearly 1 million hospital admissions for acute decompensated CHF occur in the United States yearly, almost double the number seen 15 years ago. The rehospitalization rates during the 6 months following discharge are as high as 50%. Nearly 2% of all hospital admissions in the United States are for decompensated CHF, and heart failure is the most frequent cause of hospitalization in patients older than 65 years. The average duration of hospitalization is about 6 days. An estimated $23 billion are spent on inpatient management of CHF every year, and another $40 billion are spent in the outpatient setting on patients with compensated or mildly decompensated heart failure every year. Despite aggressive therapies, hospital admissions for CHF continue to increase, reflecting the prevalence of this malady.

Heart transplants have been the gold standard of treatment for end-stage CHF. A heart transplant is the replacement of a diseased heart with a healthy one from an organ donor. Candidates for transplant have irreparably damaged hearts, are facing imminent death, and have otherwise viable vital organs. Transplanted hearts generally fail 9.5 years (on average) after implantation. The American National Heart, Lung, and Blood Institute estimated that as many as 100,000 Americans would benefit from a transplant each year. Of these, fewer than 8,000 are ever placed on the national transplant waiting list, and only 2,000 to 2,500 hearts become available for transplantation. Most patients spend months or years waiting for a suitable donor heart and die before one becomes available. As of December 2006, 40,363 heart transplants have been performed in the United States. Nearly 85% of transplant recipients survive over one year following the procedure, and 70% survive for over 5 years. Over 3,000 transplants are performed worldwide each year, including 2,125 in the U.S. in 2005.

A ventricular assist device (VAD), is an electro-mechanical device that is used to partially or completely replace the function of a failing heart. Some VADs are intended for short term use, typically for patients recovering from heart attacks or heart surgery, while others are intended for long term use (months to years and in some cases for life), typically for patients suffering from CHF. VADs need to be clearly distinguished from artificial hearts, which are designed to completely take over cardiac function and generally require the removal of the patient's heart. VADs are designed to assist either the right (RVAD) or left (LVAD) ventricle. The choice of device depends on the underlying heart disease and the pulmonary arterial resistance which determines the load on the right ventricle. LVADs are most commonly used but when pulmonary arterial resistance is high, right ventricular assist becomes necessary. Long term VADs are normally used to keep patients alive with a good quality of life while they wait for a heart transplant.

Most VADs operate on similar principles. A cannula is inserted into the apex of the appropriate ventricle. Blood passes through this to a pump and thence through a tube to the aorta in the case of an LVAD or to the pulmonary artery in the case of an RVAD. The pump is powered through a lead which connects it to a controller and power supply. The first generation VADs, like the one described in U.S. Pat. No. 4,906,229, emulate the heart by using a pulsatile action where blood is alternately sucked into the pump from the left ventricle then forced out into the aorta. These devices are usually cumbersome and necessitate major surgery for their implantation into the vascular system and for introducing the cannula into the heart ventricule. More recent devices are based on intravascular continuous flow pumps, which can be roughly categorized as either centrifugal pumps, like in US 2004/0143151 which is now U.S. Pat. No. 7,470,246, or axial flow impeller driven pumps, like in U.S. Pat. No. 4,957,504. These second generation VADs have impellers with high flow rate capability and are much smaller than the first generation VADs, but have contacting bearings that suspend the rigid motor. The bearing contacts generally cause undesirable clot formation either inside or around the periphery of the bearings, making these devices unsuitable for long-term use. In these pumps, blood experiences traumatisation and damage due to shearing and vortexing into the small gaps between the outer edge of the stator blades and the inner side of the pipe carrying blood. Latest generation VADs overcome these issues by suspending the impeller in the pump using either hydrodynamic or electromagnetic suspension. therefore decreasing risks of thrombosis or hemolysis. Such pumps are described for example in U.S. Pat. No. 6,527,699 or US 2004/0115038 which is now U.S. Pat. No. 7,467,929.

Superposition—

The superposition theorem for electrical circuits states that the response (Voltage or Current) in any branch of a bilateral linear circuit having more than one independent source equals the algebraic sum of the responses caused by each independent source acting alone, while all other independent sources are replaced by their internal impedances.

To ascertain the contribution of each individual source, all of the other sources first must be "killed" (set to zero) by: replacing all other independent voltage sources with a short circuit (thereby eliminating difference of potential. i.e. V=0, internal impedance of ideal voltage source is ZERO (short circuit)).
replacing all other independent current sources with an open circuit (thereby eliminating current. i.e. I=0, internal impedance of ideal current source is infinite (open circuit).

Dependent sources are untouched.

This procedure is followed for each source in turn, then the resultant responses are added to determine the true operation of the circuit. The resultant circuit operation is the superposition of the various voltage and current sources.

The superposition theorem is very important in circuit analysis. It is used in converting any circuit into its Norton equivalent or Thevenin equivalent.

Applicable to linear networks (time varying or time invariant) consisting of independent sources, linear dependent sources, linear passive elements Resistors, Inductors, Capacitors and linear transformers.

SUMMARY OF THE EMBODIMENT

One or more aspects of a method for treating biological tissue substantially according to any feature or combination of features described below.

A treatment method comprising introducing, into the descending aorta, a mechanical pump whose electrical power source is wireless. The mechanical pump is introduced into by a non-surgical catheterization procedure.

The mechanical pump that we suggest is special by the constant blood flow thru the pump. This goal is achieve by the combination of one or more of the:
  i) the mechanical and/or electrical properties of the pump for instant more screw in the axial flow pump increase the pump independence and reduce the effect of the changing pressure that cause by the heart; and/or
  ii) the location and/or orientation of the pump; and/or
  iii) the presence of one or more additional foreign objects within the aorta for instant balloon or covered stent that close the aorta and force the blood to the pump only; and/or
  iv) the result of one or more aorta modification procedures to modify a shape of the aorta;
causes the rate of blood flow within the aorta to be substantially constant and/or substantially independent of the heart cardiac cycle. For example flow rate of 3 liter per minute is a good goal and if it is constant it will relax the heart like smaller cycle, just as current sources replace with an open circuit The Aorta blocking and fixation is done using a foreign object. The foreign object is a stent and/or a balloon.

A treatment method comprising introducing one or more foreign object(s) into a host artery selected from the group consisting of the aorta, renal artery, and the femoral artery such that operation of the foreign object(s) within the host object causes the rate of blood flow within the aorta to be substantially constant and/or substantially independent of the cardiac cycle. wherein one of the foreign object(s) can be a mechanical pump.

To allow the pump to work in the aorta it's electrical power source should be wireless. This patent suggest efficient method to do it using external power transfer belt and internal receiver. The internal receiver should us all the aorta diameter. This can be achieve using a balloon or expendable stent to expend the coils diameter.

A kit for a Endovascular ventricular assist device (EVAD) comprising:
  i) one axial flow pump
  ii) a power receiver;
  iii) an external power belt;
  iv) a mechanical fixation and blocking component
  v) a controller unit;
  Characterized in that said EVAD are configured to allow them to be implanted inside a blood vessel without surgery, and use wireless power harvesting.
the fixing and or blocking in the aorta is using a balloon that covers the pump or using a stent for fixation and or for blocking forcing the blood to path thru the pump only. The fixation method can also be use as power harvesting receiver. By separate stents or by a weave stent that the receiver coil can use the stent wires for power harvesting Some embodiments of the present invention provide one or more (i.e. any combination of) of the following features:
  This patent suggest technique for wireless pump located in the descending aorta and help the heart
  It is the main revolution of using this patent for solution of VAD that work in serial to the heart, using the correct calculation of superposition in order to find the suitable pump.
  It is also embodiment of this invention to suggest methods that enable Endovascular VAD implementation of VAD pump using catheterization procedure only, with no need for surgery the VAD inserted into the descending aorta using catheter then installed and powered from out side the body using power belt
  This invention suggest example for pump installation and fixing in the aorta.
  Power belt that supply power to VAD like in 3 using digital control signaling from the VAD to the Belt controller or simply control the VAD function by sensing the magnetic or electrical field changes
  EVAD like in 3 fixing in the aorta using a balloon that covers the pump
  EVAD like in 3 fixing in the aorta using A basket careful design to generate steady flow that not sensitive to potential
  EVAD like in 3 fixing using metal material as extended magnetic core for the power transfer
  EVAD like in 3 implementing efficient power transfer methods that use direct frequency that can be use to generate AC engine of VAD.
  It is also embodiment of this patent to suggest methods that enable permanent VAD solution using surgery, yet simply migrate from the EVAD like in 3 temporal catheterization procedure using small belt/ring of power transmitter inject into the patient chest surrounding the aorta this replace the external belt After the patient recover with more robustness and power efficiency.

BRIEF DESCRIPTION OF THE DRAWINGS

FIG. 1—electrical circuits that resemble the human vascular system

FIG. 2—The heart supply only to the upper body—the main organ

FIG. 3—the lower body organs

FIG. 4—Human vascular system with pump

FIG. 5—powered from out side the body using coil as power receiver

FIG. 6—powered from out side the body using power belt
FIG. 7—Cardio Bridge location
FIG. 8—Cardio Bridge Pump
FIG. 9—longer fixation example done on pigs using PUMP located in the descending aorta (Table 1) we actually fine that the heart Echo reflect relaxation in the heart activity. Yet the actual flow runs thru the heart increase dramatically.

TABLE 1 test result done on pigs using PUMP located in the descending aorta

| Pump Flow per minute | Heart Rate | Blood Pressure Systole | Blood Pressure Diastole | Mean Blood Pressure | Saturation O2 | Echo-End Diastole Volume | Echo-End Systole Volume | LVEF [%] Ventricular Ejection Fraction | CO− Cardiac Output | SW− Stroke Work | CO+ Pump Flows |
|---|---|---|---|---|---|---|---|---|---|---|---|
| No Pump | 84 | 121 | 90 | 100 | 100 | 110 | 57.1 | 48.1% | 4.44 | 5.3 | 4.4 |
| 1.2 Liter, | 72 | 140 | 105 | 117 | 99 | 129. | 63.3 | 51.3% | 4.79 | 7.7 | 5.9 |
| 2 Liter, | 75 | 128 | 85 | 99 | 99 | 111. | 57 | 48.8% | 4.08 | 5.4 | 6.0 |
| 2.5 Liter, | 75 | 128 | 90 | 103 | 95 | 104. | 59.8 | 42.9% | 3.36 | 4.6 | 5.8 |
| 3.2 Liter, | 76 | 117 | 75 | 89 | 99 | 90.1 | 48.3 | 46.4% | 3.17 | 3.7 | 6.3 |
| 4.2 Liter, | 76 | 112 | 69 | 83 | 97 | 88.5 | 60.3 | 31.9% | 2.14 | 2.3 | 6.3 |
| 5 Liter, | 75 | 108 | 61 | 77 | 96 | 70.9 | 46.7 | 34.1% | 1.81 | 1.8 | 6.8 |
| 5 Liter, | 73 | 138 | 101 | 113 | 96 | 108. | 76.3 | 29.8% | 2.36 | 3.6 | 7.3 |

FIG. 10—Magnetic capability & fixation
FIG. 11—fixation and power receiver option
FIG. 12—extract the coil to aorta dimension
FIG. 13—The relation between the coils diameter to the receiver capability
FIG. 14—The three stages of stent installation
FIG. 15—One Weave stent that use some of its wire as power receiver
FIG. 16—migration from Vertical magnetic power to tri Horizontal AC motor coils
Table 1—test result done on pigs using PUMP located in the descending aorta

DETAILED DESCRIPTION OF THE EMBODIMENT

VAD that Use the Superposition Theory:

Adding new pump to the human body is a superposition problem and understanding this objective is the source for this problem solving. Today Most of the VAD are located in the chest sucking the blood from the heart apex to the ascending Aorta. The equivalent to the heart & the VAD pump mutual work is two power source in parallel the heart is basically not working at all and the all work is done by the pump.

Using different architecture by locating the pump in aorta changes this topology and result in more complex equation.

If we translate this information to the vascular blood system the electrical circuits that resemble the human vascular system look like FIG. 1. When we assume (to make it simple) the heart is more like Voltage source and the Pump in this picture act like current source. The nature of the pump change depends on the pump technique! Therefore it is critical to understand this solution theory and mathematical background. The superposition calculation of this example show that the heart work only to supply the needed of the upper body. Assuming that the pump should be treated as a disconnection.

The Pump work reflect mainly on the lower body organs as it can be understand from FIG. 3. And the lower organ can get as sufficient amount of blood as it needed. The heart supply only to the main organs—the upper organs as can see in FIG. 2

This is the best result we can expect from any partial VAD located in the descending aorta. And if we look at test result If we change the Pump from current source to voltage source we get poor result. We do change the flow to the legs and kidney but the heart itself keeps work hard. The VAD Pump as voltage source treated as a short when we calculate the heart work and we actually don't relaxant the heart at all. We do receive better perfusion to the lower body but it can't replace and help failing heart for long time.

If we use peristaltic pump that more then any other pump resemble current source or practically axial flow pump that with the correct amount of springs act as a good current source we get real relief on the heart.

Understanding this background allow us to suggest more limited solution like more partial assist for the kidney—the result will be relief to the kidney and if we use the right pump technique relief to the heart also.

This Patent Suggest Two Technique that Enable the First Use of VAD Located in the Descending Aorta that Work in Serial to the Heart Also some initiation was made in the direction of using VAD in the Aorta like Abiomed device—Impella. The main barriers for creating VAD from this technique are—the power & control connection and the right mathematical background and simple model to calculate correctly the pump's added value and behavior this patent suggest the first answer to this barrier using the correct calculation of superposition help to find the suitable pump.

It just likes the new sound projector that calculates the sound that the user hears and projects it especially for him. They are totally different from regular stereo systems. The same revolution is offering to calculate the right pumping behavior instead for just putting pump in the descending aorta. We can look at U.S. Pat. No. 5,749,855 of Cardio Bridge for instant, it suggest to implement temporal assist device using catheter in the descending aorta but without understanding of the mathematical theory of adding new pump to the vascular system. The pump they suggest describe in FIG. 7 and in FIG. 8 of cardio bridge pump.

Due to the lack of understanding the superposition principle they use a ventilator like pump. The pump resembles more then any other pump a Voltage source. As a Voltage source the main pump—the heart treat the vascular system just as it was before—a short. And we won't find any change in the heart work.

The added pump model should be as close as possible to current source model in order to really relax the heart Other advantage of using the superposition model allow us to locate the pump in the renal artery or in the femoral (from many reasons like complexity) and yet to calculate exactly the added value that we give to the hear work Therefore the patent is on the way of using pump correctly and the right basic and primitive calculation that enable efficiently use of Pump in the aorta in order to help failing heart It is Also Embodiment of this Invention to Suggest Methods that Enable Endovascular Implementation of VAD Pump Using Catheterization Procedure Only, with No Need for Surgery. The VAD Inserted into the Descending Aorta Using Catheter, then Installed and Powered from Out Side the Body Using Power Belt See FIGS. 5 and 6.

Unlike prior art like Intra Aortic Balloon Pump and Impella catheter pump or Cardio Bridge U.S. Pat. No. 5,749,855—the VAD install in the descending aorta and stay their. The catheter is use for the insertion only and can be remove. The pump also can be removed in catheterization. And the power supply use wireless technique It is Also Embodiment of this Invention to Suggest Example for Pump Installation and Fixing in the Aorta.

One of the optional fixing methods is using a balloon that covers the pump and get with the pump in the catheterization procedure. When reach it's location the balloon filled with saline. Using strong valve the balloon keep the saline and stay filled. When it get remove the balloon simply porous.

A basket can be used for pump fixation with more careful design. The basket use for total fixation can't just expend & hold the pump—it need longer fixation like in FIG. 9

Also the technique used in the IVC filter for fixation and removal are proper technique to use for pump fixation in the aorta and it can be used along or with one of the other technique It is also embodiment of this invention to suggest Power belt that supply power to VAD like in FIGS. 5 and 6 using digital control signaling from the VAD to the Belt controller or simply control the VAD function by sensing the magnetic or electrical field changes It is Also Embodiment of this Invention to Suggest Example for Using the Installation Material as Extended Magnetic Core for the Power Transfer It can be see in FIG. 10 that the fixing metal can be use for extending the magnetic core. The use of ferrite is the most common in electro magnetic device. Some materials are better then ferrite, and can be use also for the installation and fixation materials.

It is Also Embodiment of this Patent to Suggest Methods that Enable Permanent VAD Solution Using Surgery, Yet Simply Migrate from the Above Temporal Catheterization Procedure After the heart condition and the patient parameters improve a small belt/ring of power transmitter inject into the patient chest surrounding the aorta this replace the external belt with more robustness and power efficiency.

This suggestion complimenting PCT/IL2008/000604 (which is now WO 2008/135988A2) and suggest starting with catheterization procedure treating the patient in his critical condition. And after the patient condition get stable migrate to longer time solution using internal belt as describe in PCT/IL2008/000604 (which is now WO 2008/135988A2).

It is Also Embodiment of this Invention to Suggest Efficient Power Transfer Methods that Use the Entire Aorta Diameter for the Receiving Coils Use external belt for power transfer into the body need good efficiency in the receiver side. The efficiency depend on the entire regular well know technique as the core permeability and the coils diameter and more. When inserting the power receiver in catheterization process the diameter is force to be as limited to the femoral artery diameter. The suggested technique is to connect the coils wire to the fixation mechanism and expend the coil in the target aorta location (it can be a balloon or other fixation like IVC filter or stent) FIGS. 11, 12, 13 show simple use cases of using coil extraction and compare to regular coil in the insertion diameter. The improvement is by 25 time from the insertion diameter!

It is Also Embodiment of this Invention to Suggest Efficient Power Transfer Methods that Use Special Stent as a Power Receptor. The Stent can be Use for Power Harvesting and Fixation.

The basic power harvesting can be perform using selected wire in the stent process that suitable for coils. The main difficulty is this simple offer is that the stent flexibility and fixation are weak.

Using multi layer stents is an option. Inserting the stents one after the other when one is regular flexible stent and the other are electromagnetic special one. In this option one stent is used for fixation one for power harvesting and one as a ferrite using ferromagnetic material. FIG. 14 describe the insertion process when starting with insertion of a fixation stent then insertion of the power harvesting stent and last the ferrite stent.

It can even be more economic or simple installation catheterization process, using one weaving base stent or mesh-weave stents for more then one aim. Allow using part of the weaving wire as a receptor coils and the other for fixation and/or ferromagnetic propose (as improving ferromagnetic or as Freddy cage) FIG. 15 describe a mesh-weave stent that part of the weave wire are suitable for power harvesting. The weaving technique allows wide variety of wire selection and a huge flexibility. This enables electromagnetic capable stents for power harvesting, shielding and nerve stimulation.

The Last Two Embodiments are not Unique to VAD.

They are most applicable in all power transfer technologies or Freddy Cage.

These embodiments allow using a special mix of wire in the weave adding electromagnetic capabilities to traditional stent.

The multi layer stent can contribute in other manner as drug insertion or covered stents. Allowing covered stent simple development adding a fixation stent as multi layer It is Also Embodiment of this Invention to Suggest Efficient Power Transfer Methods that Use Direct Frequency that can be Use to Generate AC Engine of VAD.

The AC engine use tri phase or one phase and capacitors. FIG. 16 describe simple migration from Vertical magnetic power to tri Horizontal AC motor coils. It can use frequency Division or multiplexing. This is direct use of magnetic field that reduces the power loss in transformation.

It is further noted that any of the embodiments described above may further include receiving, sending or storing instructions and/or data that implement the operations described above in conjunction with the figures upon a computer readable medium. Generally speaking, a computer readable medium may include storage media or memory media such as magnetic or flash or optical media, e.g. disk or CD-ROM, volatile or non-volatile media such as RAM, ROM, etc. as well as transmission media or signals such as electrical, electromagnetic or digital signals conveyed via a communication medium such as network and/or wireless links.

Having thus described the foregoing exemplary embodiments it will be apparent to those skilled in the art that various equivalents, alterations, modifications, and improvements thereof are possible without departing from the scope and spirit of the claims as hereafter recited. In particular, different embodiments may include combinations of features other than those described herein. Accordingly, the claims are not limited to the foregoing discussion.

The invention claimed is:

1. A method of treating a patient having a body, blood, and a descending aorta, comprising:
    introducing a pump into the patient's descending aorta;
    powering the introduced pump wirelessly by use of a power transfer belt disposed external to the patient's body; and
    using the wirelessly-powered introduced pump to move the patient's blood through the descending aorta at a substantially constant rate.

2. The method of claim 1 wherein the introducing step comprises using a catheterization procedure to introduce the pump into the patient's descending aorta.

3. The method of claim 1 wherein the pump is wirelessly powered.

4. The method of claim 1 wherein the pump is an axial flow pump.

\* \* \* \* \*